(12) United States Patent
Collins

(10) Patent No.: US 6,893,454 B2
(45) Date of Patent: *May 17, 2005

(54) INTRARECTAL HEAT EXCHANGE CATHETER

(75) Inventor: Kenneth A. Collins, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 140 days.

This patent is subject to a terminal disclaimer.

(21) Appl. No.: 10/425,681

(22) Filed: Apr. 28, 2003

(65) Prior Publication Data

US 2004/0215297 A1 Oct. 28, 2004

(51) Int. Cl.[7] ............................................... A61F 7/12
(52) U.S. Cl. ...................................... 607/113; 607/105
(58) Field of Search .......................... 607/96, 104–106, 607/113

(56) References Cited

U.S. PATENT DOCUMENTS

| | | | | |
|---|---|---|---|---|
| 3,125,096 | A | * 3/1964 | Antiles et al. | 607/105 |
| 6,126,684 | A | * 10/2000 | Gobin et al. | 607/113 |
| 6,231,594 | B1 | * 5/2001 | Dae | 607/96 |
| 6,254,626 | B1 | 7/2001 | Dobak et al. | 607/105 |
| 6,451,045 | B1 | * 9/2002 | Walker et al. | 607/105 |
| 6,530,946 | B1 | * 3/2003 | Noda et al. | 607/113 |
| 6,572,640 | B1 | * 6/2003 | Balding et al. | 607/105 |
| 6,641,602 | B2 | * 11/2003 | Balding | 607/105 |
| 2002/0151943 | A1 | 10/2002 | Balding | 607/105 |

* cited by examiner

Primary Examiner—Roy D. Gibson
(74) Attorney, Agent, or Firm—John L. Rogitz

(57) ABSTRACT

A closed loop heat exchange catheter can be placed in the rectum of a patient to cool or warm the patient.

6 Claims, 2 Drawing Sheets

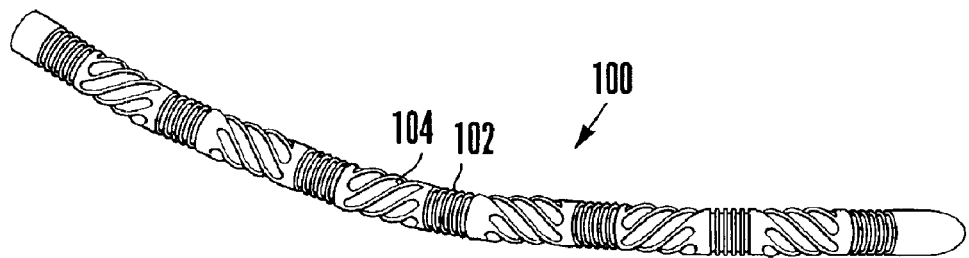
Figure 2
Figure 3
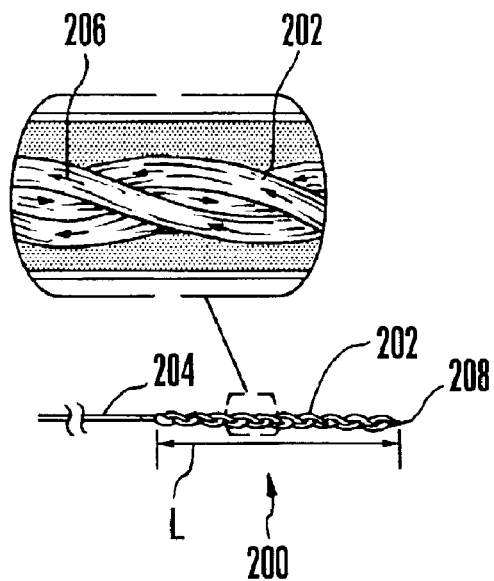

ional patents, all of which are incorporated

INTRARECTAL HEAT EXCHANGE CATHETER

FIELD OF THE INVENTION

The present invention relates generally to heat exchange catheters.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

As critically recognized by the present invention, it may be easier for some medical personnel such as emergency response teams to temporarily initiate cooling without intubating a catheter in the bloodstream.

SUMMARY OF THE INVENTION

A system for treating a patient includes a heat exchange catheter configured for placement in the rectum of a patient to induce hypothermia in the patient when heat exchange fluid is circulated through the catheter. A heat exchanger supplies heat exchange fluid to the catheter and receives heat exchange fluid from the catheter in a closed circuit. The heat exchange catheter can be coil-shaped and the heat exchange fluid can be a compressed gas.

In one embodiment, the catheter has a heat exchange portion that is established by a balloon. In other embodiments, the heat exchange portion includes plural heat exchange fluid return tubes communicating with a supply lumen at a distal end of the catheter for carrying heat exchange fluid, with each return tube being formed spirally. In yet another embodiment, the heat exchange portion includes first and second elongated segments, each segment having an irregular exterior surface, and a flexible articulating joint connecting the first and second elongated segments.

In another aspect, a method for treating a patient includes inducing hypothermia in the patient using a closed loop heat exchange catheter placed in the patient's rectum.

In still another aspect, a system for treating a patient includes closed circuit heat exchange means configured for positioning in the patient' rectum to exchange heat therewith.

The details of the present invention, both as to its structure and operation, can best be understood in reference to the accompanying drawings, in which like reference numerals refer to like parts, and in which:

BRIEF DESCRIPTION OF THE DRAWINGS

FIG. 2 is a perspective view of an alternate rectal catheter; and

FIG. 3 is a perspective view of another alternate rectal catheter, showing the distal portion of the catheter and an enlarged view of the heat exchange region.

DETAILED DESCRIPTION OF THE PREFERRED EMBODIMENT

Figure 1:
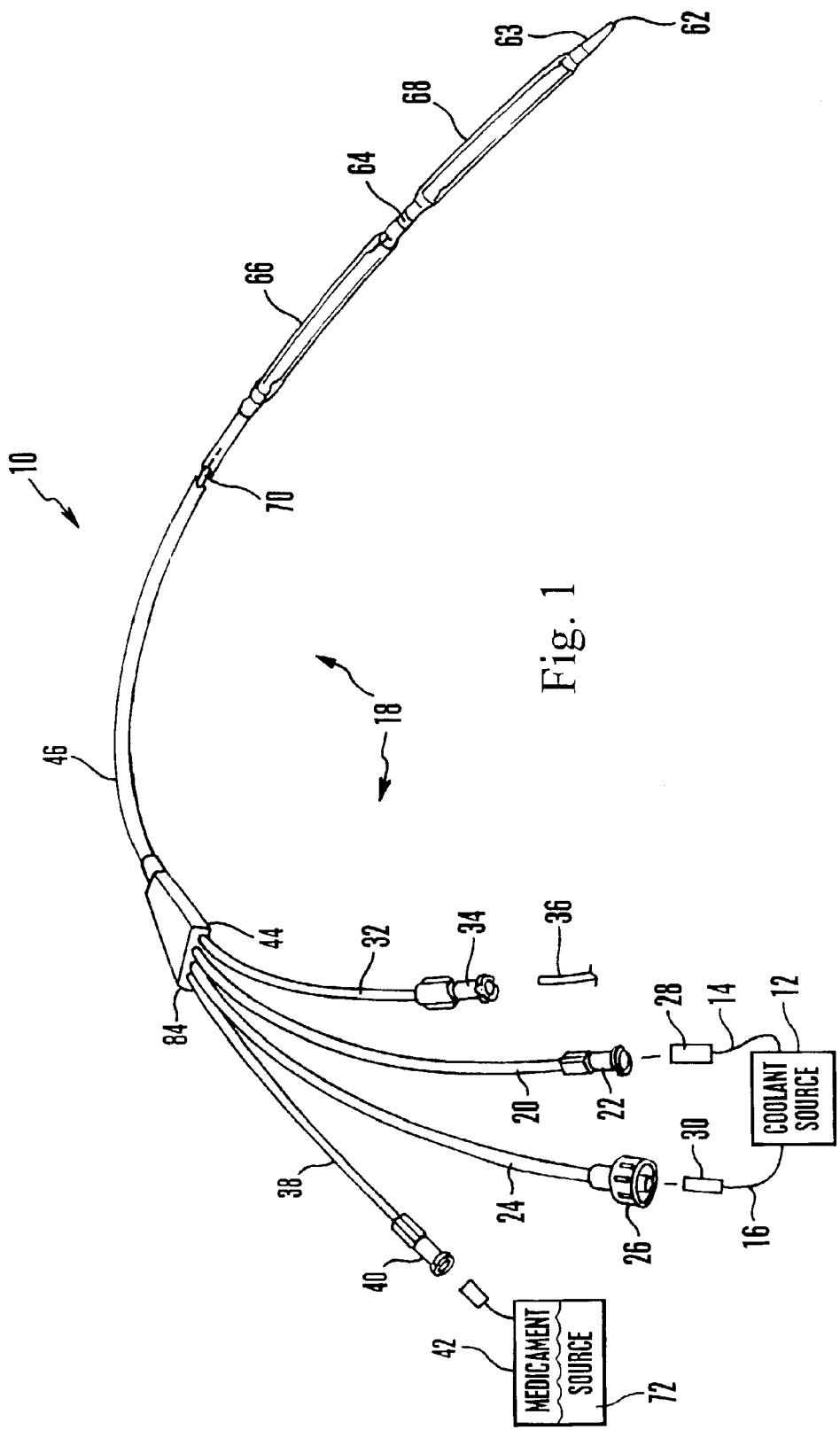
FIG. 1 is a perspective view of the present rectal heat exchange catheter, schematically showing a medicament source and heat exchange fluid source in an exploded relationship with the catheter.

Referring initially to FIG. 1, a therapeutic catheter system, generally designated 10, is shown for establishing and maintaining hypothermia in a patient, or for attenuating a fever spike in a patient and then maintaining normal body temperature in the patient. While FIG. 1 shows an exemplary embodiment of one rectal heat exchange catheter, it is to be understood that the present invention applies to any of the catheters and accompanying heat exchangers disclosed in the above-referenced patents, including the helical shaped devices disclosed in Alsius' U.S. Pat. Nos. 6,451,045 and 6,520,933. Also, one of the spiral-shaped or convoluted-shaped catheters disclosed in Alsius' co-pending U.S. patent application Ser. No. 10/234,084, filed Aug. 30, 2002, for an "INTRAVASCULAR TEMPERATURE CONTROL CATHETER", and in Ser. No. 10/355,776, filed Jan. 31, 2003, both of which are incorporated herein by reference, can be used.

Commencing the description of the system 10 at the proximal end, as shown the exemplary non-limiting system 10 includes a heat exchange fluid source 12 that can be a water-bath heat exchange system or a TEC-based heat exchange system such as any of the systems disclosed in one or more of the above-referenced patents. Or, the source 12 can be a source of compressed gas. In any case, the heat exchange fluid source provides warmed or cooled heat exchange fluid such as saline or compressed gas through a heat exchange fluid supply line 14, and heat exchange fluid is returned to the source 12 via a heat exchange fluid return line 16. A catheter, generally designated 18, includes a source tube 20 terminating in a fitting such as a female Luer fitting 22. Also, the catheter 18 has a return tube 24 terminating in a fitting such a male Luer fitting 26. The fittings 22, 26 can be selectively engaged with complementary fittings 28, 304 of the lines 14, 16 to establish a closed circuit heat exchange fluid path between the catheter 18 and heat exchange fluid source 12.

Additionally, a non-limiting catheter 18 may include a guide wire and primary infusion tube 32 that terminates in a fitting such as a female Luer 34. A guide wire 36 can be advanced through the tube 32 in accordance with central venous catheter placement principles, or medicament or other fluid can be infused through the guide wire and primary infusion tube 32. Moreover, a secondary infusion tube 38 with female Luer fitting 40 can be selectively engaged with a medicament source 42 for infusing fluid from the source 42 through the secondary tube 38 in accordance with present principles discussed below.

As discussed further below, the tubes 20, 24, 32, 38 are held in a distally-tapered connector manifold 44. As also set forth further below, the connector manifold 44 establishes respective pathways for fluid communication between the tubes 20, 24, 32, 38 and respective lumens in a catheter body 46.

In any case, the connector manifold 44 establishes a pathway for fluid communication between the heat exchange fluid supply tube 20 and the heat exchange fluid supply lumen of the catheter. Likewise, the connector manifold 44 establishes a pathway for fluid communication between the heat exchange fluid return tube 24 and the heat exchange fluid return lumen. Further, the connector manifold 44 establishes a pathway for fluid communication between the guide wire and primary infusion tube 32, and the guide wire lumen, which can terminate at an open distal hole 62 defined by a distally tapered and chamfered distal tip 63 of the catheter body 46. Also, the connector manifold 44 establishes a pathway for fluid communication between the secondary infusion tube 38 and the secondary infusion lumen, which can terminate at an infusion port 64 in a distal segment of the catheter body 46. Additional ports can be provided along the length of the catheter.

An exemplary non-limiting catheter 18 has a distally-located heat exchange member for effecting heat exchange with the patient when the catheter is positioned in the rectum of a patient. The heat exchange member can be any of the heat exchange members disclosed in the above-referenced patents. By way of example, a non-limiting catheter shown in FIG. 1 can have proximal and distal thin-walled heat exchange membranes 66, 68 that are arranged along the last fifteen or so centimeters of the catheter body 46 and that are bonded to the outer surface of the catheter body 46, with the infusion port 64 being located between the heat exchange membranes 66, 68. Thus, each preferred non-limiting heat exchange membrane is about six centimeters to seven and one-half centimeters in length, with the heat exchange membranes being longitudinally spaced from each other along the catheter body 46 in the preferred embodiment shown. Essentially, the heat exchange membranes 66, 68 extend along most or all of that portion of the catheter 46 that is intubated within the patient. The heat exchange membranes can be established by a medical balloon material.

The heat exchange membranes 66, 68 can be inflated with heat exchange fluid from the heat exchange fluid source 12 as supplied from the heat exchange fluid supply lumen, and heat exchange fluid from the heat exchange membranes 66, 68 is returned via the heat exchange fluid return lumen to the heat exchange fluid source 12.

If desired, a temperature sensor 70 such as a thermistor or other suitable device can be attached to the catheter 18 as shown. The sensor 70 can be mounted on the catheter 18 by solvent bonding at a point that is proximal to the membranes 66, 68. Or, the sensor 70 can be disposed in a lumen of the catheter 18, or attached to a wire that is disposed in a lumen of the catheter 18, with the sensor hanging outside the catheter 18. Alternatively, a separate temperature probe can be used, such as the esophageal probe disclosed in U.S. Pat. No. 6,290,717, incorporated herein by reference. As yet another alternative, a rectal probe or tympanic temperature sensor can be used. In any case, the sensor is electrically connected to the heat exchange fluid source 12 for control of the temperature of the heat exchange fluid as described in various of the above-referenced patents.

As envisioned by the present invention, the structure set forth above can be used in many medical applications to cool a patient and/or to maintain temperature in a normothermic or hypothermic patient, for purposes of improving the medical outcomes of, e.g., cardiac arrest patients, patients suffering from myocardial infarction or stroke, etc. As another example, head trauma can be treated by and after lowering and maintaining the patient's temperature below normal body temperature.

Now referring to FIG. 2, an alternate rectal catheter 100 can include plural heat exchange elements 102. The heat exchange elements 102 can be established by one or more metal, preferably gold, hollow elongated segments that have external surfaces which have irregular exterior surfaces. Separating adjacent heat exchange elements 102 can be a flexible articulating joint 104, it being understood that the heat exchange elements 102 and joints 104 can be formed from a single piece of material such as plastic or metal, e.g., gold. The details of the heat exchange elements 102 and their configuration are set forth in U.S. Pat. No. 6,096,068, incorporated herein by reference. In any case, heat exchange fluid is circulated in a closed fluid communication loop between the heat exchange elements 102 and a heater/chiller to remove heat from the patient 12 to add heat to the patient to rewarm the patient after surgery or after the termination of therapeutic hypothermia treatment. When compressed gas is used as the heat exchange fluid, the gas is directed into the catheter, where it expands to cool the catheter and, thus, the patient.

FIG. 3 shows still another alternate rectal heat exchange catheter 200. The catheter 200 shown in FIG. 3 can include plural heat exchange elements 202. The heat exchange elements 202 can be established by, e.g., three heat exchange fluid return tubes made of hollow plastic or metal, with each tube establishing a respective heat exchange fluid return lumen. A central heat exchange fluid supply lumen is established by a center tube 204. It is to be understood that the supply lumen conveys heat exchange fluid from a heater/chiller in a distal direction along the catheter 200, whereas the heat exchange elements 202 (the heat exchange fluid return tubes) convey heat exchange fluid back to the heater/chiller in a proximal direction as indicated by the arrows 206 in FIG. 3. Thus, heat exchange fluid is circulated in a closed fluid communication loop between the heat exchange elements 202 and heater/chiller to remove heat from the patient or to add heat to the patient to rewarm the patient after surgery or after the termination of therapeutic hypothermia treatment.

The heat exchange fluid return tubes are spirally formed around the center tube 204, and can be adhered thereto or not. That is, the preferred heat exchange elements 202 define spirals. The length "L" of the heat exchange region of the catheter 200 can be about 250 millimeters, with the pitch of the spiral heat exchange elements 202 being about 64 millimeters. In any case, the heat exchange fluid supply lumen terminates in a hollow distal tip 208, as do the lumens of the heat exchange elements 202. Accordingly, heat exchange fluid passes from the supply tube to the return tubes at the distal tip 208.

In operation, any one of the above-disclosed catheters is advanced (by, e.g., emergency response personnel) into the rectum of a patient diagnosed as requiring temperature control. For example, a patient may be diagnosed with cardiac arrest, stroke, acute MI, or other malady for which therapeutic hypothermia may be indicated. Or, the patient may initially be suffering from unwanted hypothermia.

To cool the patient, the heat exchange fluid is cooled to below body temperature and circulated through the catheter as needed to reach a desired set point. Or, if the heat exchange fluid is gas, the gas is directed into the catheter where it expands and cools, cooling the catheter body. To warm the patient, the heat exchange fluid is warmed to above body temperature and circulated through the catheter.

In addition to the above, the present catheter may also be used to cool victims of heat stroke. As recognized herein, such patients are both too hot and too dry, with rectal cooling having two advantages. First, cooling is applied to an area that is highly vascular. Second, the presently preferred catheter allows the infusion of physiological fluids into the rectum directly, where most water absorption occurs (specifically, in the distal bowel). Further, the present invention recognizes that the anal sphincter can provide a reasonable seal on the fluid infusion, allowing it to reside in the rectum and be absorbed.

While the particular INTRARECTAL HEAT EXCHANGE CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

I claim:

1. A system for treating a patient, comprising:
   a heat exchange catheter configured for placement in the rectum of the patient to induce hypothermia in the patient when heat exchange fluid is circulated through the catheter, wherein a distal portion of the catheter includes:
   at least first and second elongated segments, each segment having an irregular exterior surface; and
   a flexible articulating joint connecting the first and second elongated segments; and
   a heat exchanger supplying heat exchange fluid to the catheter and receiving heat exchange fluid from the catheter in a closed circuit.

2. The system of claim 1, wherein the heat exchange fluid is a compressed gas.

3. The system of claim 2, wherein a distal portion of the catheter includes at least one balloon.

4. The system of claim 2, wherein a distal portion of the catheter includes plural heat exchange fluid return tubes communicating with a supply lumen at a distal end of the catheter for carrying heat exchange fluid, each return tube being formed spirally.

5. A method for treating a patient, comprising:
   inducing hypothermia in the patient using a closed loop heat exchange catheter placed in the rectum of the patient, wherein the catheter includes plural heat exchange fluid return tubes communicating with a supply lumen at a distal end of the catheter for carrying heat exchange fluid, each return tube being formed spirally.

6. The method of claim 5, wherein the catheter includes at least one balloon.

* * * * *